United States Patent [19]
Ahsan et al.

[11] Patent Number: 5,481,357
[45] Date of Patent: Jan. 2, 1996

[54] APPARATUS AND METHOD FOR HIGH-EFFICIENCY, IN-SITU PARTICLE DETECTION

[75] Inventors: Aziz M. Ahsan, Hopewell Junction, N.Y.; Kianoush Beyzavi, Cary, N.C.; Nagaraja P. Rao, Minneapolis, Minn.

[73] Assignee: International Business Machines Corporation, Armonk, N.Y.

[21] Appl. No.: 201,732

[22] Filed: Mar. 3, 1994

[51] Int. Cl.$^6$ .................................................. G01N 21/00
[52] U.S. Cl. ............................................ 356/338; 356/246
[58] Field of Search .................................... 356/338, 246, 356/339

[56] References Cited

U.S. PATENT DOCUMENTS

| | | | |
|---|---|---|---|
| 4,174,180 | 11/1979 | Gebhart et al. | 356/338 |
| 4,358,302 | 11/1982 | Dahneke | 55/392 |
| 4,739,177 | 4/1988 | Borden | 250/574 |
| 4,746,215 | 5/1988 | Gross | 356/339 |
| 4,794,086 | 12/1988 | Kaspar et al. | 356/336 |
| 4,804,853 | 2/1989 | Borden et al. | 250/574 |
| 4,917,496 | 4/1990 | Sommer | 356/336 |
| 5,040,424 | 8/1991 | Marple et al. | 73/863.23 |
| 5,092,675 | 3/1992 | Sommer | 356/338 |
| 5,094,533 | 3/1992 | Sawada et al. | 356/338 |
| 5,132,548 | 7/1992 | Borden et al. | 250/574 |

FOREIGN PATENT DOCUMENTS

| | | | |
|---|---|---|---|
| 2701523 | 1/1977 | Germany | G01N 15/00 |
| 1261832 | 12/1988 | Japan | H01L 21/304 |
| 2015824A | 9/1990 | Spain | B01D 45/08 |

OTHER PUBLICATIONS

"Monitoring Particles in Vacuum-Process Equipment", by Peter G. Borden, PhD., et al., Microcontamination, pp. 30–34 (1987).

"Aerodynamic Focusing of Particles in a Carrier Gas", by J. Fernandez de la Mora, et al., J. Fluid Mech., pp. 1–21 (1988).

"Aerodynamic Focusing of Particles and Molecules in Seeded Supersonic Jets", by J. Feranandez de la Mora, reprinted from Rarefield Gas Dynamics: Physical Phenomena, pp. 247–277 (1989).

"Performance of the High Yield Technology, Inc., PM–100 In Situ Particle Flux Monitor", by R. Caldow, et al., Aerosol Science and Technology, 1: 981–991 (1990).

"Investigating a Prototype in Situ Particle Monitor on the Exhause Line of a CVD Reactor", by David Greenstein, et al., Microcontamination, pp. 21–26 (Mar. 1991).

"Monitoring Downstream Particles in a Single–Wafer CVD Oxide Reactor", by Jennifer E. Stern, et al., Microcontamination, pp. 17–19 (Nov. 1991).

Model 7320 Vacuum Particle Detector Product Information Sheet from TSI (1991).

*Primary Examiner*—Richard A. Rosenberger
*Attorney, Agent, or Firm*—Ira D. Blecker

[57] ABSTRACT

The present invention relates generally to a new apparatus and a method for a high-efficiency in-situ vacuum particle detection. More particularly, the invention encompasses an apparatus for a particle detecting instrument designed to detect the presence of gas-borne particles in a vacuum line with high efficiency, using a sharply converging nozzle to preferentially focus the suspended particles flowing through it into a small region located on the nozzle axis within a few exit dimensions downstream from the nozzle exit. This focal region has a dimension much smaller than that of the nozzle exit, and is illuminated by a narrow, intense light beam. The particles passing through the illuminated focal region are detected by photodetector elements receiving light scattered from the particles. A method and an apparatus for high-efficiency, in-situ particle separation and/or measurement is also disclosed.

44 Claims, 3 Drawing Sheets

APPARATUS AND METHOD FOR HIGH-EFFICIENCY, IN-SITU PARTICLE DETECTION

FIELD OF THE INVENTION

The present invention relates generally to a new apparatus and a method for particle detection, and more particularly, the invention encompasses an apparatus and a method for high-efficiency, in-situ particle detection and/or particle separation. This invention further relates to a particle measuring and counting system and, more particularly, to a particle measuring and counting system with an improved particle sensing means having special applicability for use in a vacuum line and semiconductor processing equipment.

BACKGROUND OF THE INVENTION

Instruments for measuring particles and/or separating particles are utilized in an increasing number of situations. Perhaps the single largest field of use is in the semiconductor industry wherein cleanliness in fabricating semi-conductors is extremely important. For example, particle counters are utilized to monitor the number of particles in the so called clean rooms in which semiconductor manufacturing operations are conducted. Clean rooms are usually classified on the basis of the maximum number of particles of a given size permitted per volume of air. To meet specifications and maintain quality levels of the product being made, it is necessary to ensure that particle contamination is kept to an acceptable minimum requirement.

The basic system utilized in most airborne particle counters transmits a sample air stream through a beam of light, which results in light energy being scattered by the particles. This energy is detected and measured by suitable optics and electronics. Significant improvements have been made in the optics and electronics employed for detecting and processing the scattered light signals. Also, the advent of lasers has greatly improved the quality and intensity of the illuminating light beam.

In spite of these improvements, the accuracy of the data output from the instruments still leaves much to be desired. Tests also reveal other inaccuracies, such as recirculating particles and appreciable discrepancies in absolute count correlation between different instruments.

Others have addressed this particle detection problem by developing particle measuring systems, wherein the particles to be detected or measured are entrained in a fluid stream which is passed through a light beam, typically a laser light beam. As stated earlier, the particles passing through the beam will scatter light which is collected and focused on a photodetector or photodetectors resulting in electrical pulses being generated. The intensity of the scattered light and, accordingly, the amplitude of the pulses generated by the photo-detectors provide an indication of the particle sizes.

In many systems, it is important to detect every particle in the entrained fluid stream. This need requires that the light beam pass through the entire cross sectional area of the fluid stream entraining the particles. When the fluid stream is a liquid stream, the conduit carrying the stream through the light beam is typically narrowed down to a small cross sectional area so that a high intensity beam can be caused to pass through the entire cross sectional area of the fluid stream. When the fluid stream entraining the particles is a gas stream of substantial density, the seeded gas stream is shaped by a nozzle into the form of the sheet and a laser beam is passed through the sheet-shaped stream along its long dimension as described, for example, in U.S. Pat. No. 4,746,215 to Kenneth P. Gross. The nozzle in this device has a slowly varying cross-section that does not appreciably affect the ability of the suspended particles to closely follow the gas streamlines (i.e., no separation occurs between particles and the gas phase). However, when the particles are in vacuum, as in semiconductor processing equipment, nozzles cannot readily be used to shape the stream into a sheet-like form. In addition, in order for the vacuum line to efficiently transmit a vacuum to the work area of the semiconductor processing, it is necessary for the vacuum line to have a substantial cross sectional area. Thus, the prior art particle detecting systems involving narrow conduits or nozzles for shaping the fluid stream have limitations which make them not fully satisfactory in detecting particles in a vacuum line such as that employed in semiconductor processing equipment.

In the manufacture of semiconductor and packaging devices using thin-film technology, one of the major yield detractors is defects caused by particle contamination on the thin-film surfaces. It is now known that a major proportion of such defects are caused by particle contamination generated within the process equipment or tools used to manufacture the thin-film devices, as disclosed by Bowling, R. A., et al., "Status and needs of in-situ real-time process particle detection," J. Environ. Sci., Vol. 32(5), pages 22–27 (1989).

Much of the process equipment used in thin-film manufacture or in the semiconductor industry operates at low pressures (e.g. RIE, PECVD). For these tools, in-situ particle monitors are more frequently being used to detect and control process-equipment related contamination, and are often mounted in the process chamber exhaust line.

Presently, available vacuum line monitors generally use light scattering to detect gas-borne particles flowing through a passage, a section of which is illuminated by a laser beam perpendicular to the flow direction as discussed in Greenstein, D., et al., "Investigating a Prototype In Situ Particle Monitor on the Exhaust Line of a CVD Reactor," Microcontamination, Vol. 3, pages 21–26 (1991) and Stern, J. E., et al., "Monitoring Downstream Particles in a Single-Wafer CVD Oxide Reactor," Microcontamination, Vol. 11, pages 17–56 (1991). In these instruments, a single focused laser beam is used to illuminate a small portion of the flow passage cross-section. Only a very small fraction of the particles in the flow are illuminated and thus detected. The low detection efficiency (on the order of 0.1–3.0 percent) of such particle monitors often results in poor quality particle count statistics, thus making the monitor less useful for statistical process control (SPC) applications.

There have been a number of attempts to resolve the problem of low detection efficiency. In one case a multiply reflected beam was used to create a light "sheet" or "net" which increased the illuminated area in the vacuum conduit, as disclosed by Borden, U.S. Pat. No. 4,739,177. However, an independent study by Caldow, R., et al., "Performance of the High Yield Technology Inc. PM-100 In Situ Particle Flux Monitor," Aerosol Science Technology, Vol. 12, pages 981–991 (1990), noted only a modest increase in efficiency of a system, such as the one disclosed by Borden. Their results showed a 4.7 percent monitor counting efficiency for 6.0 micron particle size, while the efficiency for the 0.5 micron particle size was only 0.1 percent, when a multiply reflected beam system made by High Yield Technology, the assignee of Borden's U.S. Pat. No. 4,739,177, was used.

A more recent device documented in U.S. Pat. No. 5,092,675 to Sommer, uses a sheet of laser light to illuminate the entire cross-section area of the vacuum conduit, by which means every particles flowing in the conduit may be detected. This increase in the illuminated cross-section may, however, require lasers of correspondingly higher power to maintain the minimum detectable particle size at current levels.

Thus, further improvements in particle detectors or counters is needed.

The invention disclosed herein also detects particles by light scattering. However, the novel design utilizes a specially designed system that uses the light source, beam optics, photodetector elements and a unique nozzle design that aerodynamically focuses most of the suspended particles in the fluid flow into a focal region whose cross-section is small in comparison to the nozzle exit area. The focal region is illuminated by one or more narrow, intense beams of light, preferably a focused laser beam, and thus a large fraction (estimated to be close to 100 percent) of the particles in the flow can be detected. The high particle detection efficiency that can be obtained with this new invention is well suited for many industrial applications, such as, the SPC applications.

SUMMARY AND PURPOSES OF THE INVENTION

The invention is a novel method and an apparatus for detecting particles with high-efficiency and in-situ within a fluid flow.

Therefore, one purpose of this invention is to provide an apparatus and a method that will provide a high-efficiency, in-situ particle detection.

Another purpose of this invention is to provide a particle detector that will work in vacuum with high-efficiency.

Still another purpose of this invention is to provide a particle detector that will work on-line in a semiconductor process.

Yet another purpose of this invention is to provide a particle detector which has a variable nozzle to change the focal point of the particles that are being detected.

Still yet another purpose of this invention is to provide a particle detector which has a slidable means to vary the distance between the nozzle and the light beam used for detecting the particles.

In one aspect this invention comprises an apparatus for detecting particles flowing through a fluid conduit comprising in combination, a nozzle having at least one focusing means for aerodynamically focusing said particles into a focal region, wherein the cross-sectional area of said focal region is substantially smaller than the cross-sectional area of said focusing means, at least one means for illuminating said focal region with at least one narrow beam of light, and at least one means for detecting light scattered by said particles illuminated by said light beam.

In another aspect this invention comprises a method for detecting particles flowing through a fluid conduit comprising, (a) aerodynamically focusing particles to be detected with at least one focusing means into a focal region, wherein the cross-sectional area of said focal region is smaller than the cross-sectional area of said focusing means, (b) illuminating said focal region with at least one narrow beam of light, such that said light is scattered by said particles in said focal region, and (c) detecting said light that is scattered by said particles which were illuminated by said light beam, and further including counting the number of particles in the focal region detected during the step of detecting.

BRIEF DESCRIPTION OF THE DRAWINGS

The features of the invention believed to be novel and the elements characteristic of the invention are set forth with particularity in the appended claims. The figures are for illustration purposes only and are not drawn to scale. The invention itself, however, both as to organization and method of operation, may best be understood by reference to the detailed description which follows taken in conjunction with the accompanying drawings in which:

DETAILED DESCRIPTION OF THE INVENTION

When operating the detection systems to determine the number of particles in a fluid flow, such as gases or liquids, it is assumed that the particulates are suspended in the fluid. Typically, a gas or a liquid acts as a carrier to transport the suspended particles through the focus of a beam of light, such as a laser beam, that is used with the detection systems. The suspended particles scatter light that enables detection and thereby provides an indication of some of the physical characteristics of the particulates, such as, size of the particles, the number of particles, etc. This detection of particles could be for a variety of reasons, such as, to see the number or size of the particles being discharged into an environment or whether the magnitude of contamination is greater than a predetermined threshold for the given process or environment, to name a few.

Figure 1:
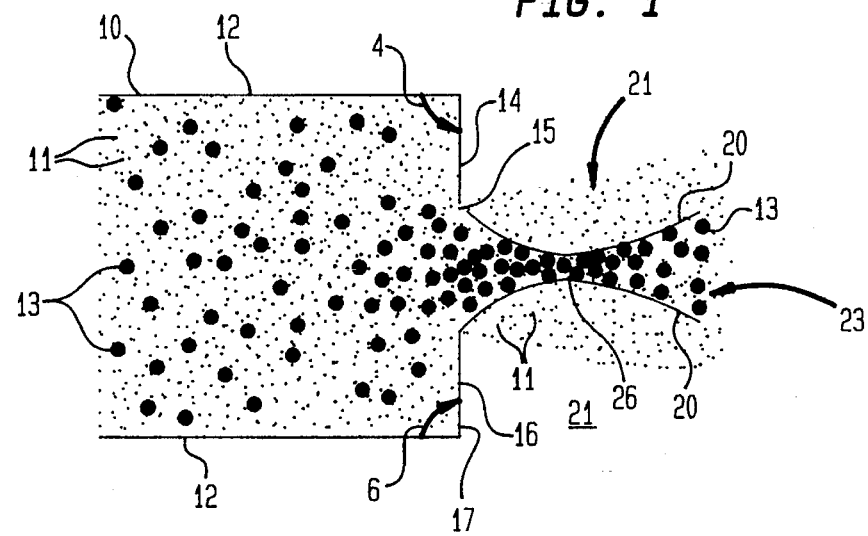
FIG. 1, illustrates a preferred fluid nozzle of this invention.

The preferred embodiment of the nozzle is shown in FIG. 1. The sharply converging nozzle 10, has a nozzle housing 12, and capped with one or more upper fixed or moveable nozzle plate 14, and one or more lower fixed or moveable nozzle plate 16. The housing of the nozzle 12, is preferably tubular, but it could be of any shape. The nozzle housing 12, has a nozzle opening or exit 15, preferably circular, to allow the fluid particles 11 and 13, to exit. For the purposes of illustration only fluid particles 11, would be sometimes referred to as a carrier fluid or gas while the fluid particles 13, will be referred to as particles to be detected or undesired particles or contaminants.

The upper plate 14, is typically at an angle 4. This angle 4, can vary between 90–135 degrees depending upon the process requirements. Similarly, the lower plate 16, is typically at an angle 6. This angle 6, can vary between 90–135 degrees depending upon the process requirements. For most operations it has been found that angles 4 and 6, should both be at 90 degrees.

The plates 14 and 16, could be of the same size or could be of a different size. Similarly, the plates 14 and 16, could be rectangular or semi-circular or any other shape. Instead of the plates 14 and 16, the nozzle 10, could be provided with a single plate 17, that has an exit or opening 15 preferably circular, for the passage of the fluid particles 11 and 13. Similarly, the plate 17, could have an opening 15, that can be varied, like an iris, to change the fluid flow characteristics. It is preferred that the angles 4 and 6, for the plate 17, are at 90 degrees, but, for some applications it may be desired to change the angles 4 and 6.

In a typical situation the fluid flow comprises one or more carrier fluids 11, that has one or more undesired particles 13, that have to be detected or counted. In a semiconductor process the carrier fluid 11, is normally a gas, such as, nitrogen, helium, hydrogen, argon, oxygen, to name a few, or a mixture of gases, and the particles 13, are some contaminating particles that were introduced typically during the semiconductor manufacturing process. The particles 13, typically have masses substantially larger than the carrier gas molecules 11.

When the fluid comprising gas and contaminating particles passes through the focussing nozzle 10, the heavier particles 13, are separated from the lighter gas particles 11, in the resulting fluid or particle-gas jet. As more clearly illustrated in FIG. 1, the fluid particles 11, converge as they approach the nozzle opening or exit 15, and then diverge soon after their passage through the opening 15, without undergoing significant compression. On the other hand, the suspended contaminating particles 13, also converge as they approach the nozzle exit or opening 15, but due to their larger momentum or inertia, they tend to retain their converging motion downstream of the nozzle opening or exit, and if sufficiently heavy, may eventually cross the jet axis at a common focal point or focal region 26. Unlike the fluid particles 11, the contaminating particles 13, are very highly compressed in the focal region 26, resulting in a very high local particle concentration in that region. The fluid flow downstream of the nozzle is thus divided into a region 23, enriched in particles 13, and in a region 21, depleted of particles 13, separated by an imaginary surface or region 20. In summary, the focussing nozzle 10, serves to preferentially funnel the heavier particles 13, through the small focal region 26, without similarly restricting the lighter gas particles 11.

A recent theoretical and experimental study by Fernandez de la Mora, J., Rossell-Llompart, J. and Riesco-Chueca, P. (1989) "Aerodynamic Focusing of Particles and Molecules in Seeded Supersonic Jets," from Rarefied Gas Dynamics: Physical Phenomena, Muntz, E. P., Weaver, D. P., and Campbell, D. H., Eds. Vol. 117 of Progress in Astronautics and Aeronautics, A1AA, Washington D.C., has discussed the aforementioned phenomenon of preferential particle focusing in great detail. As an example, FIG. 2, page 252, of the aforementioned article by Fernandez de la Mora, et al, shows the trajectories of heavy particles seeded in a light gas when that particle-laden gas flows through a sharply converging nozzle. The particles being the heavier phase, tend to concentrate along the nozzle axis downstream of the nozzle. Particles having sufficient inertia may even cross the nozzle axis at a common crossing point or focal point, the location of which depends on the flow rate, the nozzle geometry, the particle inertia, and to some extent on the particle seeding position upstream of the nozzle. In the limit of large particle inertia, the location of the focal point is reasonably insensitive to flow and particle parameters, though a "geometric aberration" effect similar to that in optical systems may be observed for particles originating at substantially different locations upstream of the nozzle. Nevertheless, for a given nozzle operated over a wide range of flow conditions, a majority of the particle trajectories pass through the focal region whose area is typically quite small (a few percent or more) in comparison to that of the nozzle exit. The focal region 26, is typically located within a few nozzle exit dimensions downstream from the opening or exit 15, and the particle phase may be enriched by a factor up to 1000 in this region.

This phenomenon, where the particles are concentrated by virtue of their inertia being greater than that of the carrier fluid has been strictly termed "aerodynamic focusing" in the technical literature. See for example, Fernandez de la Mora, et al., supra.

FIG. 2, is a schematic diagram of a preferred embodiment of the invention. In a typical application the inventive apparatus 25, is inserted between two fluid conduit sections 32 and 34, of a flow conduit carrying the particle laden gas, and secured thereto by suitable mating or securing means 31 and 33. The fluid conduit 32, is the inlet flow conduit, while fluid conduit 34, is the outlet flow conduit.

The opening or exit 15, is preferably round for sharp focusing of the contaminating or undesired particles 13. The diameter of the opening 15, should be smaller than that of the inlet section of the nozzle 10, by a factor of at least 2. While the particles 13, approaching the nozzle 10, may be distributed arbitrarily in the carrier gas 11, their passage through the nozzle 10, causes, under suitable conditions, all the particles 13, to converge and stream through the small focal region 26, located on the nozzle axis 27. By suitably varying the nozzle geometry parameters, e.g., the diameter of the nozzle opening or exit 15, in relation to that of the inlet, the focal region 26, may be located at varying distances from the nozzle exit or opening 15. The most appropriate design for the nozzle 10, will of course depend upon the physical characteristics of the particles to be detected, the characteristics of the carrier fluid flow and the number of particles to be detected, etc..

For most applications it has been found that the focal region 26, is typically 0.5 to 3 nozzle opening or exit diameters downstream from the opening or exit. This focal region 26, which has a smaller cross-sectional area in comparison to that of the nozzle exit or opening 15, is illuminated by a high intensity focused light beam 22, having a narrowness comparable to that of the particle stream in the focal region 26. The intersection of the two foci (i.e. that of the light beam 22, and that of the particle stream 13) result in the detection and/or counting of the contaminating particles 13. Using this inventive apparatus it is estimated that a particle detection efficiency of close to 100 percent is reached, which is very much higher than that which is currently possible in similar instruments not having the focusing nozzle.

The narrow light beam 22, such as, a laser beam, is produced using a light source 18, preferably a laser diode, and suitable collimating optics 28, may be used to focus the light beam 22, into the focal region 26. Part of the scattered light is collected by a light detector 19, preferably a solid-state photodetector, or photomultiplier tube, using the receiving optics 29. The incident light beam is terminated at a light stop 24, which in forward scatter configuration is shown in FIG. 2. This light stop 24, also prevents the incident beam 22, from reaching the detector 19, so that the detector 19, detects only the scattered light from the particles. The particles 11 and 13, passing through the inventive apparatus 25, is typically exhausted through the outlet flow conduit 34, using a pump.

Figure 2:
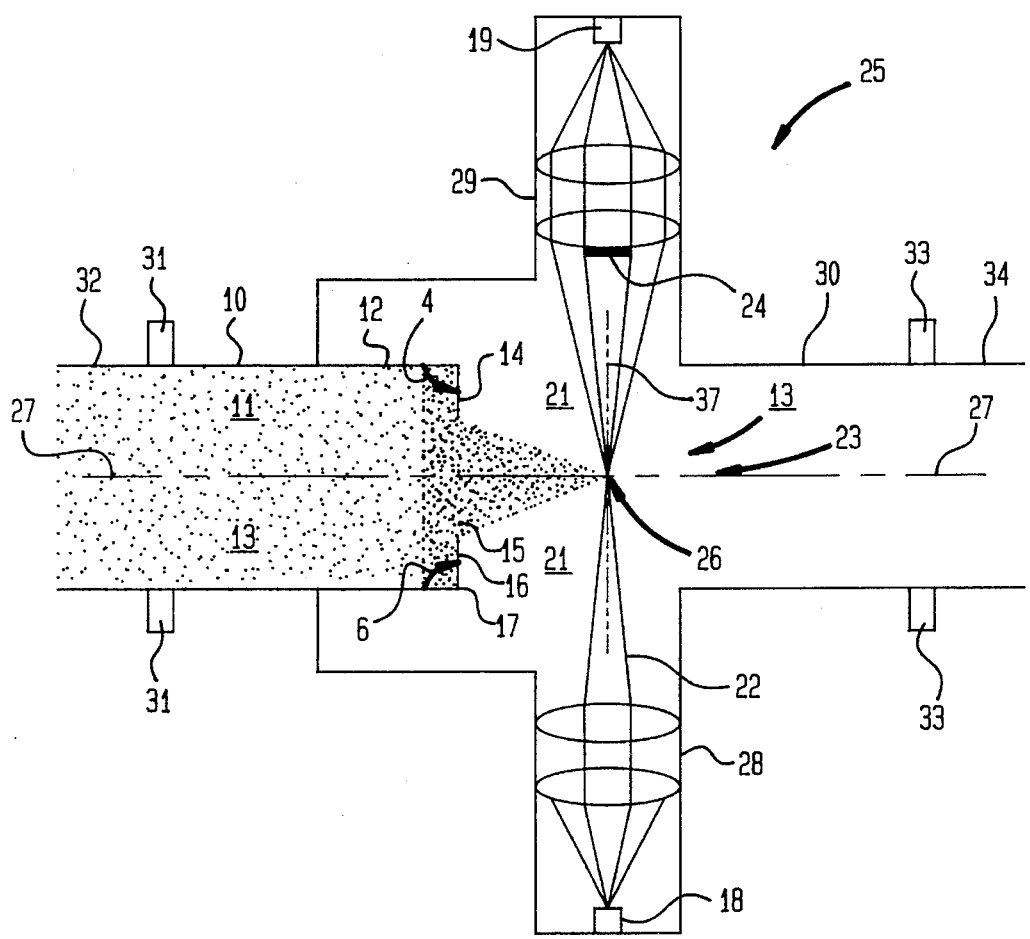
FIG. 2, is a schematic diagram of the preferred embodiment of the invention where the light beam is substantially transverse to the fluid flow through the nozzle.

As can be clearly seen in FIGS. 1 and 2, the maximum concentration of the particles 13, that have to be counted is in the focal point region 26. Therefore, in order to obtain the count for the maximum concentration the nozzle axis 27, and the optical axis 37, should intersect at a 90 degree angle so that the optical beam focus optimally intersects the particle focus.

The dimensions of the opening 15, of the sharply converging nozzle 10, from where the fluid exits, is typically smaller than that of the conduit, yet large in comparison to the thickness of the focusing light beam 22. This allows the vacuum to be efficiently transmitted through the nozzle without undue restriction.

For most applications it is preferred that the detecting optics and the exiting fluid particles are contained within a housing 30. The housing 30, would also protect the focal region 26, from outside or external influences, such as, movement in the surrounding air, light from an extraneous source, etc.

Figure 3:
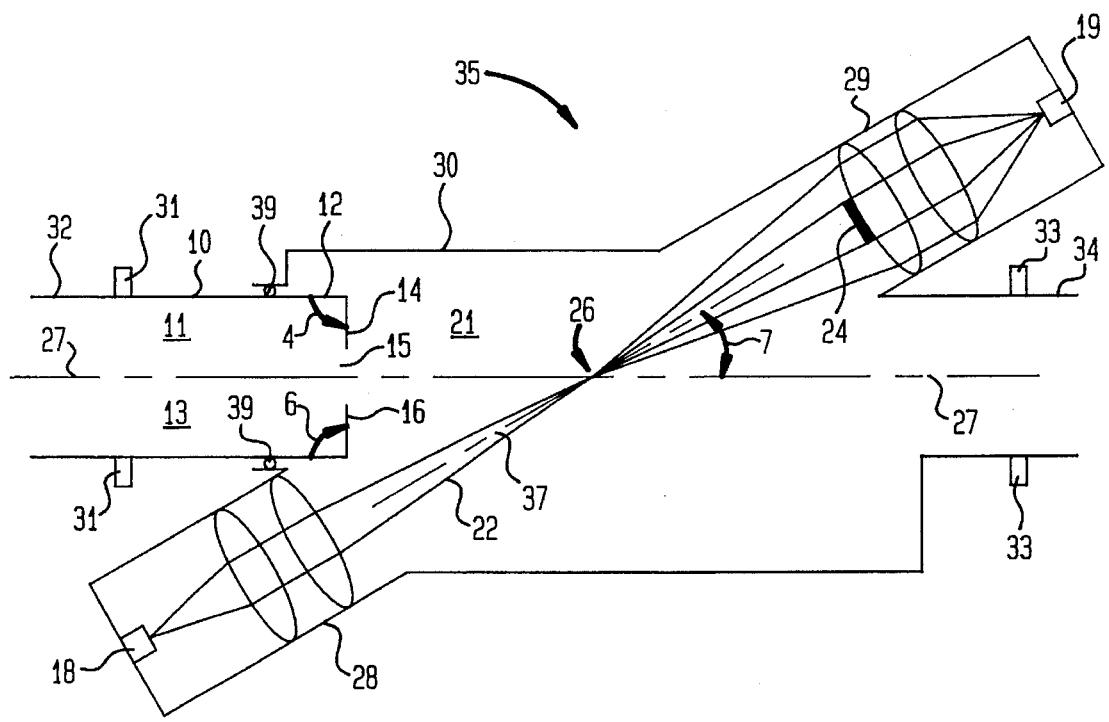
FIG. 3, is a schematic diagram of another embodiment of the invention in which the light beam is substantially coaxial with the flow through the nozzle.

Another preferred embodiment of this inventive apparatus is shown in FIG. 3. The inventive apparatus 35, is very similar to the inventive apparatus 25, except that the light source 18, is aligned substantially coaxially with the nozzle 10. When the angle of intersection 7, between the nozzle axis 27, and light beam axis 37, is small, a longer portion of the nozzle axis is illuminated. In the extreme case, the light beam 22, may be coaxial with the nozzle 10. This embodiment is less sensitive to geometric aberration effects that may cause particles 13, that are exiting the nozzle 10, to cross the axis at slightly varying distances from the nozzle exit 15.

As illustrated in FIG. 3, the distance between the nozzle exit or opening 15, and the axis of light beam 37, could be varied. This could be done by, for example, mounting the nozzle 10, on a suitable moving means 39, such as, bearings, that allow the nozzle 10, to move in the axial direction or allows the optical housing 30, to move in the axial direction. Similarly, telescopic type arrangements could be used to move either the nozzle 10, or the optical system, or both, to obtain the desired results.

Figure 4:
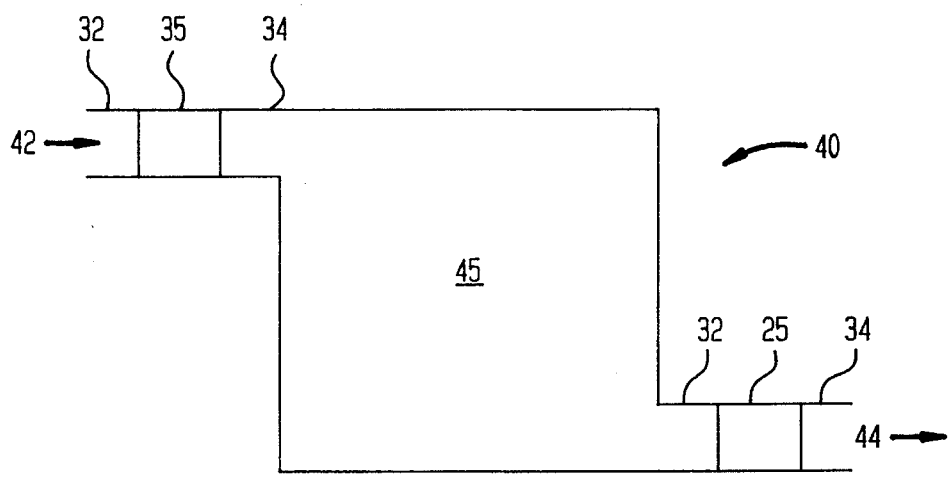
FIG. 4, is a schematic diagram of another embodiment of the invention illustrating an industrial process utilizing this invention.

FIG. 4, is a schematic diagram illustrating an industrial process utilizing this invention. A processing apparatus 40, having a processing chamber 45, has a process fluid inlet 42, and a process fluid outlet 44. As shown in FIG. 4, the apparatus of this invention could be placed either at the fluid inlet area 42, or fluid outlet area 44, or both. In order to obtain an accurate count of the particles being introduced into the fluid stream as a result of the activities in the processing chamber 45, it would be advisable to place the inventive detection system both at the fluid inlet section 42, and fluid outlet location 44. Again, care should be taken that the inventive particle detectors are placed sufficiently far from the processing chamber 45, so that these particle detectors do not have any adverse effect on the processes that are taking place inside the chamber 45.

This invention also comprises an apparatus and method for high-efficiency, in-situ particle detection and/or separation. The invention allows for high-efficiency separation and/or measurement of particles, particularly particles that are gas-borne. Many industrial applications have a need for such an invention, such as, but not limited to, semiconductor industry, pharmaceutical industries, environmental industry, etc. Perhaps the single largest field of use is in the semiconductor industry wherein cleanliness in fabricating semiconductors is extremely important, and this invention would not only allow for the measurement of particles but also the separation of desired or undesired particles. Similarly, in the pharmaceutical industry, it is a desire to separate particulates so that some of the drugs could be prepared in a particulate form. In the environmental applications, sampling and concentration of dilute environmental aerosols could be obtained for further analysis. Of course, there are many devices that are currently used for separating particles from a gas stream, such as filters and impactors. These devices typically collect particles on the surface of flow obstructing elements. However, this invention provides not only the in-situ measurement of the flowing particles but also a very high-efficiency separation of the same particles.

Figure 5:
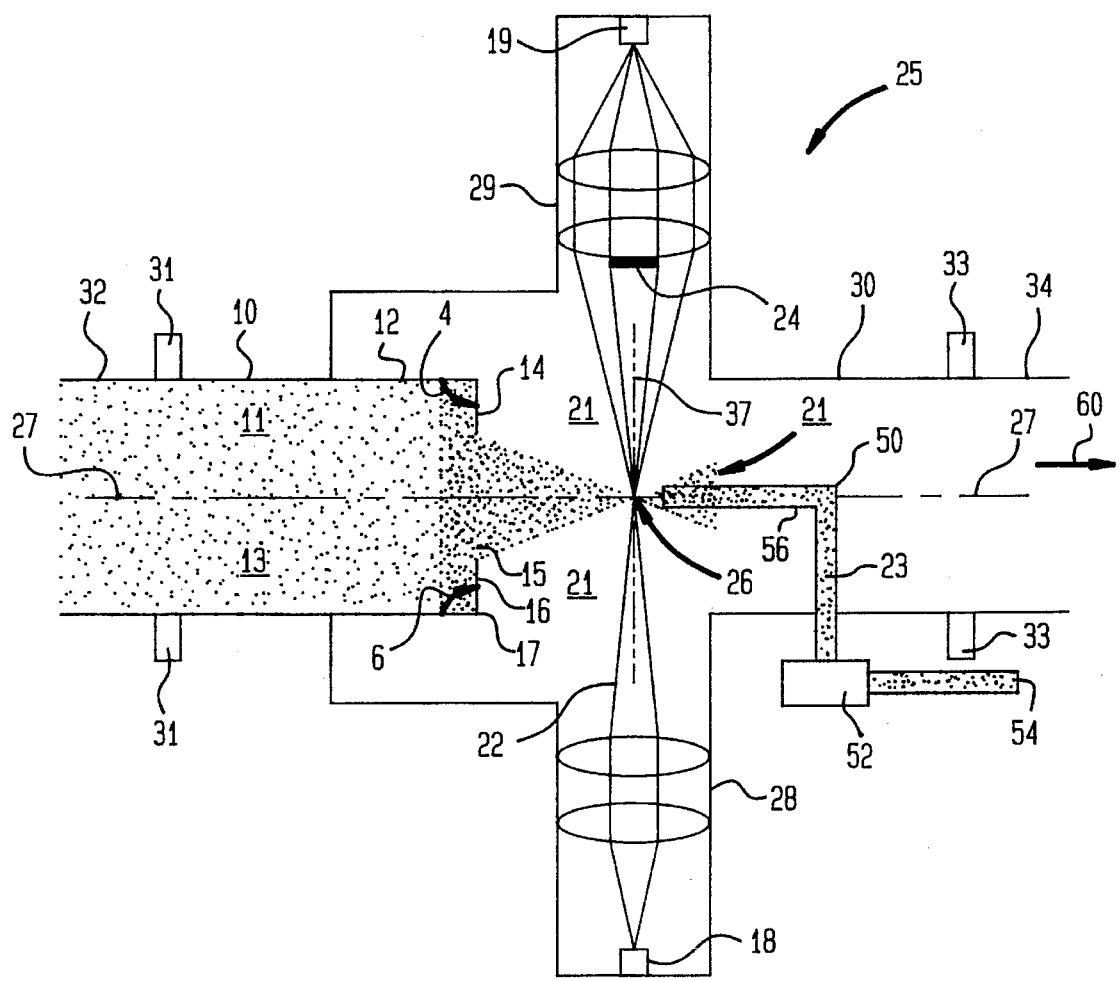
FIG. 5 is a schematic diagram of another embodiment of the invention in which there is a collector for removing particles from the fluid stream.

The invention utilizes a nozzle 10, aligned with a collector or means or probe 50, which is downstream of the nozzle 10, as shown in FIG. 5. Typically, the flow through the nozzle 10, is subsonic, and thus the flow exiting the nozzle 10, need not discharge into vacuum. Under suitably chosen flow conditions, the nozzle 10, aerodynamically converges or focuses the particles 13, in the flow into a focal area or region 26, having a size smaller in comparison to the nozzle exit dimensions. The probe 50, used typically has an inlet that is substantially smaller than the exit dimension of the nozzle 10. The probe 50, is preferably aligned with the nozzle axis and located so that it is close to or is overlapping the particle focal region 26. A small portion of the core gas flow exiting the nozzle 10, considerably enriched in particles due to focusing, is drawn or sampled through the probe 50, while the remainder, which is typically "clean" carrier gas 60, is exhausted along the outside walls of the probe 50. The flow through the probe 50, is preferably isokinetic, i.e., the gas or particle velocities just within the probe inlet are matched with the flow velocities just upstream of the probe. Isokinetic sampling is generally useful in reducing particle losses to the probe walls, which is typically not possible in the instruments of the prior art because of the large diameters of the collecting orifices, as they are usually larger then the nozzle exit.

As shown in more detail in FIG. 5 there is a collector or means or probe 50 for removing particles 13 from the fluid flow. The removal means 50 is positioned at or near focal region 26. In this manner, the fluid in the particle enriched region 23, of the fluid flow is removed by the removal means 50, while the fluid in the particle depleted region 21 of the fluid flow substantially bypasses the removal means 50, and exits as "clean" carrier gas 60. The proximity of the removal means 50, to the focal region 26, will determine the extent to which the fluid in the enriched region 23 of the fluid flow is removed. The closer the removal means 50 to the focal region 26, the more the fluid in the enriched region 23 of the fluid flow will be removed. The removal means 50 may be used in conjunction with light beam 22 and associated apparatus as shown in FIG. 5 to count the particles prior to removal. Alternatively, the light beam 22 and associated apparatus may be removed and the particles merely removed and then possibly counted later on. The removal apparatus 50 may comprise tube 56 into which the fluid in the enriched region 23 flows. Due to the fact that the tube 56 intersects the fluid flow at or near the focal region 26, the cross-sectional area (or diameter) of tube or pipe 50 is less then the cross-sectional area (or diameter) of nozzle opening or exit 15. Pump 52 may be added if needed to remove the particulates. The tube 56 removes the particles 13 from the fluid conduit for further handling via conduit 54. At some point after exiting fluid conduit 34 by tube 56, the particles may be counted if desired. Similarly, the removed particulates could also be sent for further processing, such as, preparation of drugs in a particulate form or for removal of these particulates from a closed-loop system.

Of course, this invention could also be used to aerodynamically focus and separate heavier particles from the lighter particles or for further separating the already separated particles or for preferential particle focusing and/or preferential particle separation.

While it is generally advantageous to detect forward scattered light from the particles 13, the inventive apparatus is not limited to this configuration, and off-angle detection may be used as well.

For some applications it may be advantageous to use a nozzle opening 15, that is rectangular. This would create a large aspect ratio for the opening 15, so that the suspended particles 13, would be focussed when they flow through the rectangular slit, i.e., whose length is great compared to the width. In this case, the focal area 26, has a length in a direction transverse to the fluid flow, which is comparable to the slit length. The light beam 22, would thus illuminate particles along the entire length of its passage across the walls of the flow conduit.

Yet another configuration for the nozzle 10, could be a variable exit area or opening 15, to extend the use of the inventive apparatus over a greater range of pressures and flow rates. For axisymmetric geometries the variable geometry may be achieved by substituting an iris diaphragm 17, such as those used in camera apertures, in place of the plates 14 and 16. For a rectangular geometry, a variable slit opening 15, may be implemented using two coplanar plates 14 and 16, that move in the opposite directions.

This inventive apparatus can be operated under both subsonic and supersonic flow conditions. While particle focusing is observed in both subsonic and supersonic flows through such nozzles, it is generally advantageous to operate under subsonic conditions in most of the intended applications of this device. For a given pumping capacity, subsonic flows can be generally driven with larger diameter nozzles, resulting in reasonably small pressure drops across the nozzle. For subsonic flow conditions, and for pressures ranging from 0.1 torr to 10 torr, the nozzle can have an exit diameter, which for most application is preferably larger than 3 mm, while the focused laser beam has a thickness of the order of preferably 1 mm or greater, for such applications. For supersonic flows, smaller nozzle dimensions may be necessary.

While the present invention has been particularly described, in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

What is claimed is:

1. An apparatus for detecting particles flowing through a single fluid conduit comprising, a nozzle having at least one internal focusing means secured to said single fluid conduit for aerodynamically focusing said particles into a focal region, at least one means for illuminating said focal region with at least one narrow beam of light, and at least one means for detecting light scattered by said particles illuminated by said light beam.

2. The apparatus of claim 1, wherein said internal focusing means is a sharply converging nozzle.

3. The apparatus of claim 2, wherein said nozzle is substantially axisymmetric.

4. The apparatus of claim 2, wherein said nozzle is substantially rectangular.

5. The apparatus of claim 2, wherein at least a portion of the cross-sectional area of said nozzle can be varied.

6. The apparatus of claim 2, wherein the fluid flow through said nozzle is subsonic.

7. The apparatus of claim 2, wherein the distance between said nozzle and said focal region illuminated by said light beam is at least one-third of the width of said nozzle.

8. The apparatus of claim 1, wherein said light beam intersects said focal region in a substantially transverse manner.

9. The apparatus of claim 1, wherein said light beam intersects said focal region in a substantially coaxial manner.

10. The apparatus of claim 1, wherein said internal focusing means has means to vary the distance of said focal region from said internal focusing means.

11. The apparatus of claim 1, having at least one means to move said internal focusing means.

12. The apparatus of claim 1, wherein said particles to be detected are carried by at least one carrier fluid.

13. The apparatus of claim 12, wherein said at least one fluid is at least one gas.

14. The apparatus of claim 1, wherein said at least one beam of light is a laser light.

15. The apparatus of claim 1, wherein said at least one means of detecting said scattered light has at least one means to electronically calculate said scattered light.

16. The apparatus of claim 1, further comprising at least one means for removing at least a portion of said particles from said focal region and said fluid conduit, wherein said removal means is positioned at or near said focal region.

17. The apparatus of claim 16, wherein said removal means is a tube.

18. The apparatus of claim 16, further comprising at least one means to count said particles in said focal region.

19. The apparatus of claim 1, wherein the cross-sectional area of said focal region is substantially smaller than the cross-sectional area of said internal focusing means.

20. The apparatus of claim 1, wherein said at least one internal focusing means for aerodynamically focusing said particles into a focal region is sheathless.

21. A method for detecting particles flowing through a single fluid conduit comprising, (a) aerodynamically focusing particles flowing through a single fluid conduit to be detected with at least one internal focusing means secured to said single fluid conduit into a focal region, (b) illuminating said focal region with at least one narrow beam of light, such that said light is scattered by said particles in said focal region, and (c) detecting said light that is scattered by said particles which were illuminated by said light beam, and further including counting the number of particles in the focal region detected during the step of detecting.

22. The method of claim 21, wherein said internal focusing means is a sharply converging nozzle.

23. The method of claim 22, wherein said nozzle is substantially axisymmetric.

24. The method of claim 22, wherein said nozzle is substantially rectangular.

25. The method of claim 22, wherein at least a portion of the cross-sectional area of said nozzle can be varied.

26. The method of claim 22, wherein the fluid flow through said nozzle is subsonic.

27. The method of claim 22, wherein the distance between said nozzle and said focal region illuminated by said light beam is at least one-third of the width of said nozzle.

28. The method of claim 21, wherein said light beam intersects said focal region in a substantially transverse manner.

29. The method of claim 21, wherein said light beam intersects said focal region in a substantially coaxial manner.

30. The method of claim 21, wherein said internal focusing means has means to vary the distance of said focal region from said internal focusing means.

31. The method of claim 28, having at least one means to move said internal focusing means.

32. The method of claim 21, wherein said particles to be detected are carried by at least one carrier fluid.

33. The method of claim 32, wherein said at least one fluid is at least one gas.

34. The method of claim 21, wherein said at least one beam of light is a laser light.

35. The method of claim 21, wherein said at least one means of detecting said scattered light has at least one means to electronically calculate said scattered light.

36. The method of claim 21, further comprising the step of removing at least a portion of said particles from said focal region and from said conduit by positioning a removal means at or near said focal region.

37. The method of claim 36, wherein said removal means is a tube.

38. The method of claim 36, further comprising the step of counting said particles in said focal region using at least one particle counting means.

39. The method of claim 21, wherein the cross-sectional area of said focal region is substantially smaller than the cross-sectional area of said internal focusing means.

40. The method of claim 21, wherein said step of aerodynamically focusing is accomplished sheathlessly.

41. An apparatus for separating particles flowing through a single fluid conduit comprising in combination, a nozzle having at least one internal focusing means secured to said single fluid conduit for aerodynamically focusing said particles into a focal region, wherein the cross-sectional area of said focal region is substantially smaller than the cross-sectional area of said internal focusing means, and at least one means for removing said focused particles from said focal region and from said fluid conduit.

42. The apparatus of claim 41, wherein said at least one internal focusing means for aerodynamically focusing said particles into a focal region is sheathless.

43. A method for separating particles flowing through a single fluid conduit comprising, (a) aerodynamically focusing particles flowing through a single fluid conduit to be separated with at least one internal focusing means secured to said single fluid conduit into a focal region, wherein the cross-sectional area of said focal region is smaller than the cross-sectional area of said internal focusing means, and (b) removing said separated particles from said focal region and from said single fluid conduit.

44. The method of claim 43, wherein said step of aerodynamically focusing is accomplished sheathlessly.

* * * * *